(12) United States Patent
Zhang et al.

(10) Patent No.: US 12,569,522 B2
(45) Date of Patent: Mar. 10, 2026

(54) **PHARMACEUTICAL COMPOSITION COMPRISING *SUTTERELLA WADSWORTHENSIS* AND IMMUNE CHECKPOINT INHIBITORS FOR TREATMENT OF COLON CANCER**

(71) Applicant: Xiangya Hospital of Central South University, Changsha (CN)

(72) Inventors: Wei Zhang, Changsha (CN); Yongchao Gao, Changsha (CN); Li Yang, Changsha (CN); Dingding Zhou, Changsha (CN); Weihua Huang, Changsha (CN); Honghao Zhou, Changsha (CN)

(73) Assignee: Xiangya Hospital of Central South University, Changsha (CN)

( * ) Notice: Subject to any disclaimer, the term of this patent is extended or adjusted under 35 U.S.C. 154(b) by 0 days.

(21) Appl. No.: 19/227,585

(22) Filed: Jun. 4, 2025

(65) Prior Publication Data

US 2025/0302886 A1     Oct. 2, 2025

Related U.S. Application Data

(63) Continuation of application No. PCT/CN2025/083334, filed on Mar. 19, 2025.

(30) Foreign Application Priority Data

Mar. 27, 2024     (CN) ......................... 202410356830.1

(51) Int. Cl.
    *A61K 35/74*    (2015.01)
    *A61K 39/00*    (2006.01)
    *A61P 35/00*    (2006.01)

(52) U.S. Cl.
    CPC .............. *A61K 35/74* (2013.01); *A61P 35/00* (2018.01); *A61K 2039/505* (2013.01); *A61K 2039/52* (2013.01)

(58) Field of Classification Search
    CPC .............. A61K 35/74; A61K 2039/505; A61K 2039/52; A61P 35/00
    See application file for complete search history.

(56) References Cited

FOREIGN PATENT DOCUMENTS

| CN | 113287016 A | 8/2021 |
| CN | 113645981 A | 11/2021 |

(Continued)

OTHER PUBLICATIONS

German Collection of Microorganisms and Cell Cultures. "Sutterella wadsworthensis" as obtained online at dmsz.de [retrieved on Dec. 18, 2023]. Retrieved from the internet: https://web.archive.org/web/20231218081935/https://www.dsmz.de/collection/catalogue/details/culture/DSM-14016 (Year: 2023).*

(Continued)

*Primary Examiner* — Vanessa L. Ford
*Assistant Examiner* — Bailey M Morgan
(74) *Attorney, Agent, or Firm* — Cooper Legal Group LLC

(57) ABSTRACT

A pharmaceutical composition comprising an effective amount of a live strain of *Sutterella wadsworthensis* deposited under DSM No: 14016 and immune checkpoint inhibitor (ICIs) selected from the group consisting of a PD-1 monoclonal antibody, a PD-L1 monoclonal antibody, and a CTLA-4 monoclonal antibody, together with a pharmaceutically acceptable carrier, for use in the treatment of colon cancer. The therapeutic effect of the composition is enhanced, as evidenced by increased overall survival time and increased progression-free survival time. The results show that *Sutterella wadsworthensis* in the composition (Continued)

significantly improves the efficacy of ICIs in the treatment of tumors.

1 Claim, 13 Drawing Sheets

Specification includes a Sequence Listing.

(56) References Cited

FOREIGN PATENT DOCUMENTS

| | | | | | |
|---|---|---|---|---|---|
| CN | 114159475 | A | 3/2022 | | |
| WO | WO-2018064165 | A2 * | 4/2018 | ............... | C12Q 1/04 |
| WO | 2022178193 | A2 | 8/2022 | | |
| WO | 2022261382 | A1 | 12/2022 | | |

OTHER PUBLICATIONS

Notice of first Office action dated Sep. 25, 2024 in SIPO application No. 202410356830.1, 10 pages.

Retrieval report—First search dated Sep. 11, 2024 in SIPO application No. 202410356830.1, 6 pages.

Notification to Grant Patent Right for Invention dated Oct. 31, 2024 in SIPO application No. 202410356830.1, 3 pages.

Retrieval report—Supplementary search dated Oct. 16, 2024 in SIPO application No. 202410356830.1, 4 pages.

Huang J et al., "Ginseng polysaccharides alter the gut microbiota and kynurenine/tryptophan ratio, potentiating the antitumour effect of antiprogrammed cell death 1programmed cell death ligand 1 (anti-PD-1PD-L1) immunotherapy", Gut, May 18, 2021, pp. 734-745, vol. 71, Issue 04, 12 pages.

* cited by examiner

PHARMACEUTICAL COMPOSITION COMPRISING *SUTTERELLA WADSWORTHENSIS* AND IMMUNE CHECKPOINT INHIBITORS FOR TREATMENT OF COLON CANCER

CROSS-REFERENCE TO RELATED APPLICATIONS

This application is a continuation of PCT/CN2025/083334, filed Mar. 19, 2025, which claims priority of Chinese Patent Application No. 202410356830.1, filed on Mar. 27, 2024. The entire contents of International Application PCT/CN2025/083334 and Chinese Patent Application No. 202410356830.1 are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:

File name: SequenceListing.xml
Creation date: Sep. 10, 2025
Byte size: 3,579

TECHNICAL FIELD

The present disclosure relates to the field of cancer treatment, and in particular relates to a pharmaceutical composition comprising *Sutterella wadsworthensis* and immune checkpoint inhibitors (ICIs) for the treatment of colon cancer.

BACKGROUND

Malignant tumors are a class of fatal and difficult-to-treat major diseases. Recent studies have found that ICI therapy may significantly prolong the survival of patients with various solid tumors such as non-small cell lung cancer, melanoma, and renal cell carcinoma. However, only about 30% of patients show definitive clinical efficacy to ICI therapy, while about 60-70% of patients experience primary or secondary resistance. Therefore, identifying biomarkers for ICI response, elucidating the biological mechanisms, and developing treatment regimens that may significantly enhance ICI sensitivity are of great clinical significance.

Exploring biomarkers that determine the clinical efficacy of ICIs using multi-omics (genomics, transcriptomics, epigenomics, metabolomics, and microbiomics) and designing reasonable ICI combination therapies are key to improving the overall therapeutic effect of ICIs, and are also one of the key research directions in the fields of pharmacogenomics and personalized precision therapy. Programmed cell death-ligand 1 (PD-L1) expression is currently the most commonly used biomarker for predicting ICI efficacy. High PD-L1 expression has been found to be associated with higher objective response rates in patients with non-small cell lung cancer, melanoma, and renal cell carcinoma receiving programmed death 1 (PD-1) monoclonal antibodies. However, PD-L1 does not apply to all of the cancer, and its use as a predictive biomarker for ICI efficacy is only applicable to some cancer patients. The spatial heterogeneity of PD-L1 expression and its dynamic evolution with the immune microenvironment reduce its reliability as a biomarker for ICI therapy.

The gut microbiome has become one of the potential biomarkers for predicting tumor response to ICI therapy. In preclinical models and clinical tumor patients, the gut microbiome has been shown to be significantly correlated with ICI efficacy. Studies have shown that broad-spectrum antibiotics may cause gut microbiota disruption in patients with non-small cell lung cancer and melanoma receiving ICI therapy, leading to a significant shortening of overall survival (2 months vs. 26 months, hormone receptor (HR)=7.4) and a significant increase in non-response rates. The high alpha diversity of the gut microbiota has been proven to be associated with prolonged progression-free survival in melanoma patients receiving ICI therapy. Fecal microbiota transplantation from patients who achieved complete remission (R) after PD-1 monoclonal antibody treatment to non-remission (NR) patients with end-stage metastatic melanoma resulted in approximately 30% of recipient patients (NR) showing new clinical responses, with 10% even achieving complete remission. High abundance of *Fusobacterium nucleatum* (*F. nucleatum*) in the intestine is associated with a good response to PD-1 monoclonal antibody in patients with colorectal cancer. *Bifidobacterium pseudolongum* (*B. pseudolongum*) isolated from mice with a good response to ICI therapy in situ colon cancer may enhance the anti-colorectal cancer effect of PD-1 monoclonal antibodies through its metabolite creatinine. It may be seen that the gut microbiota has an important impact on the efficacy of ICI therapy for malignant tumors such as colorectal cancer, melanoma, and non-small cell lung cancer. Specific gut microbiota may become a new class of biomarkers for predicting ICI therapy response.

The gut microbiota and its metabolites may improve ICI therapy response by regulating the innate and adaptive immunity of the body. In terms of innate immune regulation, the gut microbiota may affect the functions of dendritic cells (DCs), mononuclear macrophages, and natural killer cells (NK). For example, *Akkermansia muciniphila* (*A. muciniphila*) may activate the Toll-like receptor 2/nuclear factor kappa-B (TLR2/NF-κB) and Recombinant NLR Family, Pyrin Domain Containing Protein 3 (NLRP3) pathways and induce macrophage polarization towards M1 type, thereby inhibiting colon cancer progression. *Lactobacillus rhamnosus* GG (*L. rhamnousus* GG, LGG) activates the cyclic GMP-AMP synthase/stimulator of interferon genes/TANK-binding kinase 1/interferon regulatory factor 1 (cGAS/STING/TBK1/IRF1) signaling pathway in DCs to induce interferon-0 (IFN-0) secretion, improving the anti-tumor effect of PD-1 monoclonal antibodies. In terms of adaptive immune regulation, the gut microbiota may affect the activity of CD8$^+$T and CD4$^+$T cells. The gut microbiota metabolite butyrate enhances the tumor-killing effect of CD8$^+$T cells through the inhibitor of DNA binding 2 (ID2)-interleukin-12 (IL-12). The secondary metabolite inosine of *Bifidobacterium pseudolongum* (*B. pseudolongum*) activates the cAMP response element-binding protein (pCREB) phosphorylation through the T cell specific adenosine A2A receptor-cAMP-Plakophilin 4 (A2AR-cAMP-PK4) signaling pathway, upregulates recombinant interleukin 12 receptor beta 2 (IL12RD2) and interferon-γ (IFN-γ) transcription, and activates T helper 1 (Th1) cell immune response, thereby enhancing the efficacy of ICIs. Therefore, in-depth exploration of the functional characteristics of different types of gut microbiota and their metabolites is crucial for identifying the mechanisms of anti-tumor immune therapy responses and improving ICI efficacy.

SUMMARY

An objective of the present disclosure is to provide a pharmaceutical composition comprising *Sutterella wadsworthensis* and ICIs for the treatment of colon cancer. The combined use of *Sutterella wadsworthensis* with ICI in a composition significantly improves the therapeutic effect of ICI in treating tumors.

To achieve the above objectives, the present disclosure provides the following solutions.

The present disclosure provides a pharmaceutical composition comprising *Sutterella wadsworthensis* and ICIs for the treatment of colon cancer.

The treatment of the tumor includes tumor volume reduction or stabilization, prolonged overall survival time of tumor patients, prolonged progression-free survival, and improved quality of life.

Optionally, the *Sutterella wadsworthensis* contains a 16S rDNA sequence. The *Sutterella wadsworthensis* according to the present disclosure refers to any strain with at least 99% identity to the 16S rDNA sequence of *Sutterella wadsworthensis*. Further optionally, the *Sutterella wadsworthensis* is a combination of one or more strains of *Sutterella wadsworthensis*. Further optionally, the strain of the *Sutterella wadsworthensis* is a combination of one or more of the following strain names of subspecies classification in the genome database (https://www.ncbi.nlm.nih-.gov/genome/browse/#!/prokaryotes/ Sutterella%20wadsworthensis) of the National Center for Biotechnology Information (NCBI) in the United States: *Sutterella wadsworthensis* DSM 14016, *Sutterella wadsworthensis* FDAARGOS_1159, *Sutterella wadsworthensis* 351h, *Sutterella wadsworthensis* 809h, *Sutterella wadsworthensis* 351h, *Sutterella wadsworthensis* DFI.4.78, *Sutterella wadsworthensis* 934h, *Sutterella wadsworthensis* MCC752, *Sutterella wadsworthensis* 239h, *Sutterella wadsworthensis* 333h, *Sutterella wadsworthensis* 228h, *Sutterella wadsworthensis* 1122h, *Sutterella wadsworthensis* HGA0223, *Sutterella wadsworthensis* 3_1_45B, *Sutterella wadsworthensis* 2_1_59BFAA, *Sutterella wadsworthensis* min17_bin46, *Sutterella wadsworthensis* CD33_MAG38, *Sutterella wadsworthensis* UB A11514, *Sutterella wadsworthensis* UB A11458, *Sutterella wadsworthensis* UBG025, *Sutterella wadsworthensis* SUG770, *Sutterella wadsworthensis* 1017h, *Sutterella wadsworthensis* 1045h, *Sutterella wadsworthensis* 2733h, *Sutterella wadsworthensis* 3358, *Sutterella wadsworthensis* 876h, *Sutterella wadsworthensis* 831h, *Sutterella wadsworthensis* 856h, *Sutterella wadsworthensis* 830h, *Sutterella wadsworthensis* 877h, *Sutterella wadsworthensis* 910h, *Sutterella wadsworthensis* 627h, *Sutterella wadsworthensis* UBA10685, and *Sutterella wadsworthensis* 823h. Further optionally, the strain of the *Sutterella wadsworthensis* is a combination of one or more of the following strains: *Sutterella wadsworthensis* deposited in the German Collection Ofmicroorganism and Cell Collection (DSM) in Germany with the deposit number DSM 14016 (NCBI:taxid 40545, https://www.ncbi.nlm.nih-.gov/datasets/taxonomy/tree/?taxon=40545), *Sutterella wadsworthensis* deposited in the American Type Culture Collection (ATCC) in the United States with the deposit number ATCC 51579, *Sutterella wadsworthensis* deposited in the Japan Collection of Microorganisms (JCM) in Japan with the deposit number JCM 32440, *Sutterella wadsworth-*

*ensis* deposited in the Korean Collection for Type Cultures (KCTC) in Korea with the deposit number KCTC 15691, *Sutterella wadsworthensis* deposited in the Culture Collection University of Gothenburg (CCUG) in Sweden with the deposit number CCUG 69352, *Sutterella wadsworthensis* deposited in the Culture Collection University of Gothenburg (CIP) in France with the deposit number CIP 104799, *Sutterella wadsworthensis* deposited in the National Collection of Type Cultures (NCTC) in the United Kingdom with the deposit number NCTC 12926, and *Sutterella wadsworthensis* deposited in the Guangdong Microbial Culture Collection Center (GDMC) with the deposit number GDMC 1.2562. As an embodiment of the present disclosure, *Sutterella wadsworthensis* with the deposit number DSM 14016 is used as an example for explanation.

The ICI is a combination of one or more of the blockers acting on T cell negative co-stimulatory (co-inhibitory) molecules and/or their respective ligands. Further optionally, the T cell negative co-stimulatory (co-inhibitory) molecules and/or their respective ligands are selected from CTLA-4, PD-1, PD-L1, PD-L2, B7-1, B7-2, B7-H3, B7-H4, B7-H6, A2AR, IDO, TIM-3, B-cell Lymphoma 2-Associated Protein 3 (BTLA), VISTA, TIGIT, LAG3, CD40, KIR, carcinoembryonic antigen related cell adhesion molecule 1 (CEACAM1), GARP, PS, CSF1R, CD94/NKG2A, TDO, TNFR, and DcR3. Further optionally, the blockers of the ligands of the T cell negative co-stimulatory (co-inhibitory) molecules are selected from nivolumab (PD-1 monoclonal antibody), ipilimumab (CTLA-4 monoclonal antibody), pembrolizumab (PD-1 monoclonal antibody), atezolizumab (PD-L1 monoclonal antibody), atezolizumab (PD-L1 monoclonal antibody), camrelizumab (PD-L1 monoclonal antibody), tislelizumab (BGB-A317), durvalumab (PD-L1 monoclonal antibody), tremelimuab (CTLA-4 monoclonal antibody), spartalizumab (PD-L1 monoclonal antibody), avelumab (PD-L1 monoclonal antibody), sintilimab (PD-1 monoclonal antibody), toripalimab (PD-L1 monoclonal antibody), cemiplimab (PD-1 monoclonal antibody), MGA012 (retifanlimab, PD-1 monoclonal antibody), MGD013 (tebotelimab, PD-1/LAG-3 bispecific antibody), MGD019 (PD-1/CTLA-4 bispecific antibody), enoblituzumab (B7-H3 monoclonal antibody), MGD009 (B7-H3 monoclonal antibody), MGC018 (B7-H3 monoclonal antibody), MEDIO680 (PD-1 monoclonal antibody), PDR001 (PD-1 monoclonal antibody), FAZ053 (PD-L1 monoclonal antibody), TSR022 (TIM-3 monoclonal antibody), MBG453 (TIM-3 monoclonal antibody), relatlimab (BMS986016, LAG-3 monoclonal antibody), LAG525 (LAG-3 monoclonal antibody), IMP321 (LAG-3 monoclonal antibody), REGN3767 (LAG-3 monoclonal antibody), pexidartinib (CSF-1R monoclonal antibody), LY3022855 (CSF-1R monoclonal antibody), FPA008 (CSF-1R monoclonal antibody), BLZ945 (CSF-1R monoclonal antibody), GDC0919 (navoximod, IDO inhibitor), epacadostat (IDO inhibitor), indoximid (IDO inhibitor), BMS986205 (IDO inhibitor), CPT-444 (A2AR inhibitor), MEDI9447 (oleclumab, CD73 inhibitor), PBF509 (A2AR inhibitor), and lirilumab (KIR inhibitor), or any combination thereof. Further optionally, the blocker is selected from nivolumab, pembrolizumab, toripalimab, sintilimab, cemiplimab, or any combination thereof. Further optionally, the ICI is a blocker of the PD-1/PD-L1 signaling pathway and/or the PD-1/PD-L2 signaling pathway, where PD-1 refers to programmed cell death protein 1, also known as CD279, and PD-L1 (B7-H1 or CD274) and PD-L2 (B7-DC or CD273) are ligands of PD-1. Further optionally, the inhibitor of the PD-1/PD-L1 signaling pathway or PD-1/PD-L2 signaling pathway is selected from nivolumab (PD-1 monoclonal antibody), pembrolizumab (PD-1 monoclonal antibody), atezolizumab (PD-L1 monoclonal antibody), atezolizumab (PD-L1 monoclonal antibody), camrelizuman (PD-L1 monoclonal antibody), tislelizumab (BGB-A317), durvalumab (PD-L1 monoclonal antibody), spartalizumab (PD-1 monoclonal antibody), avelumab (PD-L1 monoclonal antibody), sintilimab (PD-1 monoclonal antibody), toripalimab (PD-1 monoclonal antibody), cemiplimab (PD-1 monoclonal antibody), MGA012 (retifanlimab, PD-1 monoclonal antibody), MGD013 (tebotelimab, PD-1/LAG-3 bispecific antibody), MGD019 (PD-1/CTLA-4 bispecific antibody), MEDI0680 (PD-1 monoclonal antibody), PDR001 (PD-1 monoclonal antibody), FAZ053 (PD-L1 monoclonal antibody), or any combination thereof. Further optionally, the ICI is an inhibitor acting on the CTLA-4/B7-1 signaling pathway and/or the CTLA-4/B7-2 signaling pathway, where CTLA-4 refers to cytotoxic T-lymphocyte protein 4, also known as CD152, and B7-1 (CD80) and B7-2 (CD86) are ligands of CTLA-4. Further optionally, the inhibitor is selected from ipilimumab (CTLA-4 monoclonal antibody), tremelimumab (CTLA-4 monoclonal antibody), MGD019 (PD-1 and CTLA-4 bispecific antibody), or any combination thereof. As a specific embodiment of the present disclosure, the ICI is an inhibitor acting on the PD-1/PD-L1 signaling pathway and/or the PD-1/PD-L2 signaling pathway and/or an inhibitor acting on the CTLA-4/B7-1 signaling pathway and/or the CTLA-4/B7-2 signaling pathway. Specifically, the ICI is a PD-1 monoclonal antibody or a CTLA-4 monoclonal antibody.

Optionally, the tumor includes tumor volume reduction or stabilization, prolonged overall survival time of tumor patients, prolonged progression-free survival, and improved quality of life.

Optionally, the tumor is an adenoma, malignant tumor, or adenocarcinoma. The tumor is classified according to tissue origin or cell name, including one or more of: bladder urothelial carcinoma, adrenocortical carcinoma, breast cancer, pancreatic cancer, cervical cancer, cholangiocarcinoma, colon cancer, colorectal cancer, diffuse large B-cell lymphoma, glioblastoma multiforme, glioma, head and neck cancer, chromophobe renal cell carcinoma, mixed neuronal cancer, renal cell carcinoma, leukemia, lymphoma, brain cancer, liver cancer, lung adenocarcinoma, lung squamous cell carcinoma, mesothelioma, ovarian cancer, pancreatic cancer, pheochromocytoma, paraganglioma, prostate cancer, rectal adenocarcinoma, sarcoma, skin melanoma, gastric cancer, esophageal cancer, testicular cancer, thyroid cancer, thymic cancer, endometrial cancer, uterine sarcoma, uveal melanoma, and soft tissue sarcoma. In a specific embodiment of the present disclosure, the tumor is colorectal cancer. Optionally, the tumor is a malignant tumor, metastatic tumor, or non-metastatic tumor. Further optionally, the tumor includes any stage of cancer (clinical stages I, II, III, or IV, tumor node metastasis (TNM) classification of malignant tumors as T1-4, NO-4, or MO-1, histological grades G1, G2, G3, or G4, etc.).

Optionally, the Sutterella wadsworthensis is a combination of one or more strains of Sutterella wadsworthensis (as described above). As an embodiment of the present disclosure, a deposit number of Sutterella wadsworthensis is DSM NO: 14016, and the ICIs include a PD-1 monoclonal antibody, a PD-L1 monoclonal antibody, or a CTLA-4 monoclonal antibody.

Optionally, the pharmaceutical composition or the preparation uses the Sutterella wadsworthensis as an active component, and the Sutterella wadsworthensis is a live bacterium.

The pharmaceutical composition further includes pharmaceutically acceptable carriers and excipients. The term "pharmaceutically acceptable" refers to molecular entities and compositions that do not produce adverse reactions, allergic reactions, or other undesirable reactions when administered to animals (e.g., humans, if appropriate). Specific examples of pharmaceutically acceptable carriers as described in the present disclosure are borate buffer or sterile saline solution.

Optionally, the pharmaceutical composition is prepared into tablets, capsules, granules, suspensions, or injections.

Optionally, the tumor includes one or more of bladder urothelial carcinoma, adrenocortical carcinoma, breast cancer, pancreatic cancer, cervical cancer, cholangiocarcinoma, colon cancer, colorectal cancer, diffuse large B-cell lymphoma, glioblastoma multiforme, glioma, head and neck cancer, chromophobe renal cell carcinoma, mixed neuronal cancer, renal cell carcinoma, leukemia, lymphoma, brain cancer, liver cancer, lung adenocarcinoma, lung squamous cell carcinoma, mesothelioma, ovarian cancer, pancreatic cancer, pheochromocytoma, paraganglioma, prostate cancer, rectal adenocarcinoma, sarcoma, skin melanoma, gastric cancer, esophageal cancer, testicular cancer, thyroid cancer, thymic cancer, endometrial cancer, uterine sarcoma, uveal melanoma, and soft tissue sarcoma.

The present disclosure further provides a pharmaceutical composition or a preparation for treating tumors, including an effective dose of Sutterella wadsworthensis in combination with an ICI, where a deposit number of Sutterella wadsworthensis is DSM NO: 14016, and the ICI includes a PD-1 monoclonal antibody, a PD-L1 monoclonal antibody, or a CTLA-4 monoclonal antibody.

The present disclosure proposes a combination therapy: the use of Sutterella wadsworthensis simultaneously, separately, or sequentially with ICI therapy to increase the therapeutic effect of ICIs.

The administration method of using Sutterella wadsworthensis is oral.

The sequence of the combination therapy is: using the Sutterella wadsworthensis simultaneously, before, and/or after ICI therapy.

In the combination therapy, dose delays and/or dose reductions and time adjustments are performed as needed based on the tolerance of the individual patients to the treatment.

The Sutterella wadsworthensis discussed in the present disclosure may contain an effective amount of Sutterella wadsworthensis typically dispersed in pharmaceutically or pharmacologically acceptable carriers.

The term "pharmaceutically or pharmacologically acceptable" refers to molecular entities and compositions that do not produce adverse reactions, allergic reactions, or other undesirable reactions when administered to animals (e.g., humans, if appropriate). Specific examples of pharmacologically acceptable carriers as described in the present disclosure are borate buffer or sterile saline solution.

The ICIs discussed in the present disclosure may be used in ICI-refractory patients, where the ICI-refractory patients exhibit innate (primary) resistance to the ICI therapy, manifested as a lack of response or insufficient response to the checkpoint inhibitor therapy from the first dose for at least about 8 weeks or 12 weeks.

The ICIs discussed in the present disclosure may be used in ICI-refractory patients, where the ICI-refractory patients exhibit acquired (secondary) resistance to the checkpoint inhibitor therapy, manifested as an initial response to the checkpoint therapy but subsequent recurrence and progression of one or more tumors.

The present disclosure discloses the following technical effects.

The present disclosure relates to a combination therapy for enhancing the efficacy of ICIs, applicable to colorectal cancer and various other tumors. The present disclosure uses *Sutterella wadsworthensis* as a novel immune adjuvant in combination with ICIs for tumor treatment, achieving significant technical effects. The present disclosure provides a scientific basis for the combination therapy of bacteria and ICIs and offers a new solution for improving the clinical efficacy of ICIs by targeting the gut microbiome. The present disclosure is of great significance for improving the overall efficacy of tumor immunotherapy and promoting the translational application of pharmacomicrobiomics in personalized precision medicine.

The present disclosure significantly enhances the efficacy of ICIs against various tumors, with higher safety, prolongs the overall survival time of cancer patients, improves the response rate of cancer immunotherapy population, and expands the beneficiary population of cancer immunotherapy (ICIs) through the use of oral preparations of human symbiotic bacteria (*Sutterella wadsworthensis*), combined with ICIs, and anti-tumor immune protection response stimulated by *Sutterella wadsworthensis*.

BRIEF DESCRIPTION OF THE DRAWINGS

In order to explain the embodiments of the present disclosure or the technical solution in the prior art more clearly, the drawings needed in the embodiments will be briefly introduced below. Apparently, the drawings in the following description are only some embodiments of the present disclosure. For one of ordinary skill in the art, other drawings may be obtained according to these drawings without creative effort.

DETAILED DESCRIPTION OF THE EMBODIMENTS

Figure 1:
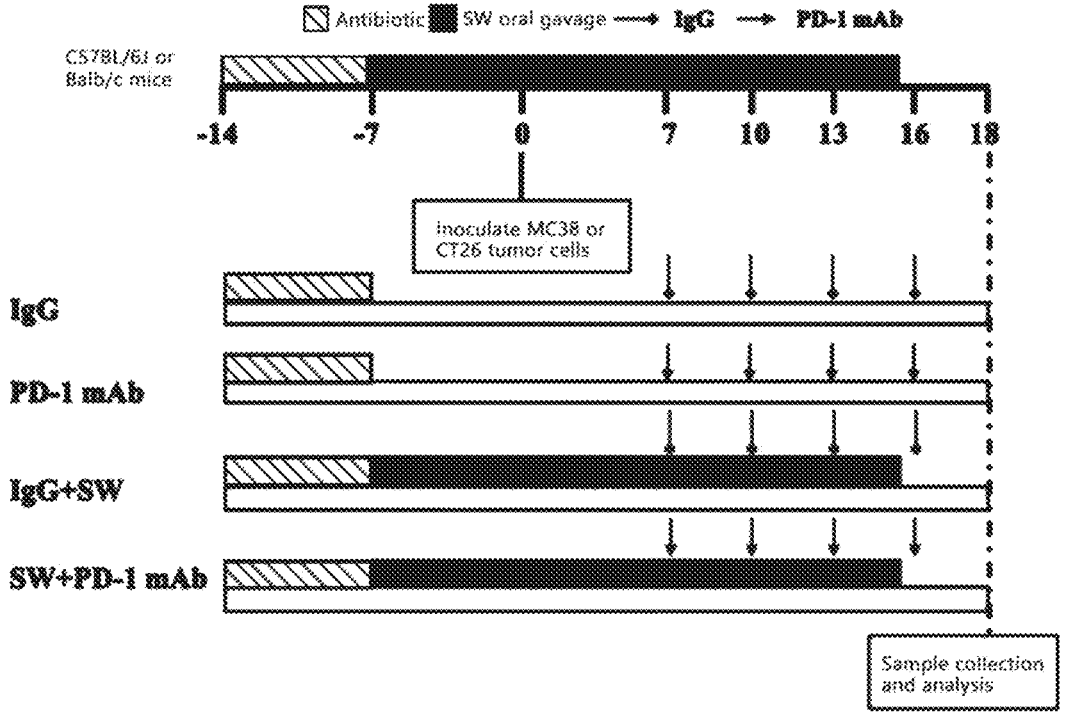
FIG. 1 is an experimental flowchart of Embodiment 1.

Various exemplary embodiments of the present disclosure are now described in detail. This detailed description should not be construed as limiting the present disclosure but should be understood as providing a more detailed description of certain aspects, features, and embodiments of the present disclosure.

It should be understood that the terms used in the present disclosure are only for describing specific embodiments and are not intended to limit the present disclosure. Additionally, for numerical ranges in the present disclosure, it should be understood that each intermediate value between the upper and lower limits of the range is also specifically disclosed. Any intermediate value within the stated range or any smaller range formed by any intermediate values within the stated range is also included in the present disclosure. The upper and lower limits of these smaller ranges may be independently included or excluded from the range.

Unless otherwise specified, all technical and scientific terms used herein have the same meanings as commonly understood by those skilled in the art to which the present disclosure pertains. Although only preferred methods and materials are described in the present disclosure, any methods and materials similar or equivalent to those described herein may also be used in the practice or testing of the present disclosure. All documents mentioned in this specification are incorporated by reference to disclose and describe methods and/or materials related to the documents. In case of any conflict with the incorporated documents, the content of this specification shall prevail.

Various modifications and changes may be made to the specific embodiments of the present disclosure described in this specification without departing from the scope or spirit of the present disclosure, as will be apparent to those skilled in the art. Other embodiments obtained from the specification of the present disclosure are also apparent to those skilled in the art. The specification and embodiments of the present disclosure are illustrative only.

Regarding the terms "comprising," "including," "having," "containing," etc., used herein, they are open-ended terms, meaning including but not limited to.

The present disclosure significantly improves the following issues: the high toxicity and side effects of conventional methods, the tendency for recurrence and metastasis, the short duration of therapeutic effects, the short survival period of patients, the economic burden, and the poor quality of life. The present disclosure also significantly improves the shortcomings of single-agent immune checkpoint therapy, such as the limited population responding to the drug and the limited types of tumors it may treat. Furthermore, the present disclosure significantly improves the shortcomings of immune checkpoint therapy combined with radiotherapy and chemotherapy, such as severe adverse reactions and the limited population responding to the drug.

The treatment regimen provided by the present disclosure has good therapeutic effects for the following patients: those who may not undergo surgery, have no effective targeted medicines available, and are ineffective with radiotherapy and chemotherapy; tumor patients who are ineffective or develop resistance (primary, adaptive, and acquired) to ICI therapy; and tumor patients who are ineffective or develop resistance (primary, adaptive, and acquired) to ICI therapy combined with radiotherapy, chemotherapy, or targeted therapy.

The following specific embodiments further illustrate the treatment regimen provided by the present disclosure.

Embodiment 1: The Therapeutic Effect of *Sutterella wadsworthensis* Combined with ICIs On Tumors 1. Experimental Methods
1.1 Experimental Materials (1) Mouse strains: 6-week-old female C57BL/6J mice and Balb/c mice.

(2) Tumor cell lines: mouse colon cancer cell line (MC38, ATCC), mouse colon cancer cell line (CT26, ATCC).

Bacterial preparation: *Sutterella wadsworthensis* (DSM NO: 14016, Type strain), abbreviated as SW, commercially available from the Deutsche Sammlung von Mikroorganismen und Zellkulturen (DSMZ) (the official website of DSMZ is: http://www.dsmz.de).

(4) Bacterial culture medium: liquid Maltase-glucoamylase (mGAM) medium, mainly composed of peptone, yeast extract, soluble starch, beef extract, and glucose, etc., commercially available from Nissui Pharmaceutical Co., Ltd., Japan. On this basis, fumaric acid (2.86 grams per liter (g/L)) and formate (2.86 g/L) are added.

(5) ICI: PD-1 monoclonal antibody (uPD-1), clone number RPM1-14, reagent purchased from BioXCell in the United States.

(6) Antibiotic combination: Ampicillin (50 milligrams per kilogram (mg/kg)), neomycin sulfate (50 mg/kg), vancomycin (25 mg/kg), metronidazole (50 mg/kg).

1.2 Experimental Grouping

The experimental groups are shown in Table 1 below.

TABLE 1

| Cell Line | Mouse Strain | Group | Number of Mice | Dose (per mouse) | Number of Treatments | Treatment Frequency |
|---|---|---|---|---|---|---|
| MC38 | C57BL/6J mice | IgG | 15 | 200 microgram (µg) | 4 times | Every 3 days |
| | | IgG + SW | 14 | IgG: 200 µg, SW: 1 × 10⁸ CFU | 4 times | IgG every 3 days, SW daily |
| | | PD-1 mAb | 13 | 200 µg | 4 times | Every 3 days |
| | | PD-1 mAb + SW | 14 | PD-1 mAb: 200 µg, SW: 1 × 10⁸ CFU | 4 times PD-1 mAb, 24 times SW | PD-1 mAb every 3 days, SW daily |
| CT26 | Balb/c mice | IgG | 7 | 200 µg | 4 times | Every 3 days |
| | | IgG + SW | 7 | IgG: 200 µg, SW: 1 × 10⁸ CFU | 4 times IgG, 24 times SW | IgG every 3 days, SW daily |
| | | PD-1 mAb | 7 | 200 µg | 4 times | Every 3 days |
| | | PD-1 mAb + SW | 7 | PD-1 mAb: 200 µg, SW: 1 × 10⁸ CFU | 4 times PD-1 mAb, 24 times SW | PD-1 mAb every 3 days, SW daily |

1.3 Experimental Methods

The experimental flowchart is shown in FIG. 1, and the specific operations are as follows.

(1) Bacterial culture: *Sutterella wadsworthensis* is inoculated in mGAM liquid medium (containing formate and fumaric acid), cultured in an anaerobic chamber at 37 degrees Celsius (° C.) for 48 hours, then centrifuged to a concentration of $1 \times 10^9$ colony-forming units per milliliter (CFU/mL).

(2) Subcutaneous inoculation of tumor cells: MC38 cell line $5 \times 10^5$ cells/mouse, CT26 cell line $5 \times 10^5$ cells/mouse.

(3) From the 14th to 8th day before tumor cell inoculation: the antibiotic combination is administered to each group of mice by gavage to clear the intestinal flora.

(4) From the 7th to 16th day before tumor cell inoculation: SW live bacterial liquid bacterial preparation treatment is administered by gavage at a rate of 100 microliter per mouse (µL/mouse), $1 \times 10^8$ colony-forming units per mouse (CFU/mouse).

(5) Immunoglobulin G (IgG) or PD-1 mAb is intraperitoneally injected at a dose of 200 microgram per mouse (µg/mouse) on the 7th, 10th, 13th, and 16th days respectively.

(6) The tumor size is measured and tumor volume is calculated on the 7th, 10th, 13th, 16th and 18th days respectively.

$$\text{Tumor volume} = (\text{tumor width}^2 \times \text{tumor length}) \times \tfrac{1}{2}$$

(7) On the 18th day, the mice are euthanized, and the tumor tissues are removed, photographed and weighed, and the gut tissues are stained with HE to confirm the intestinal inflammation.

(8) Measurement of tumor volume in mice, measurement of tumor weight at the endpoint, and evaluation of tumor tissue immune cell infiltration using multicolor flow cytometry to assess therapeutic efficacy.

(9) HE staining of mouse gut tissue sections are used to observe and assess whether *Sutterella wadsworthensis* causes enteritis for safety assessment.

2. Experimental Results

Figure 2:
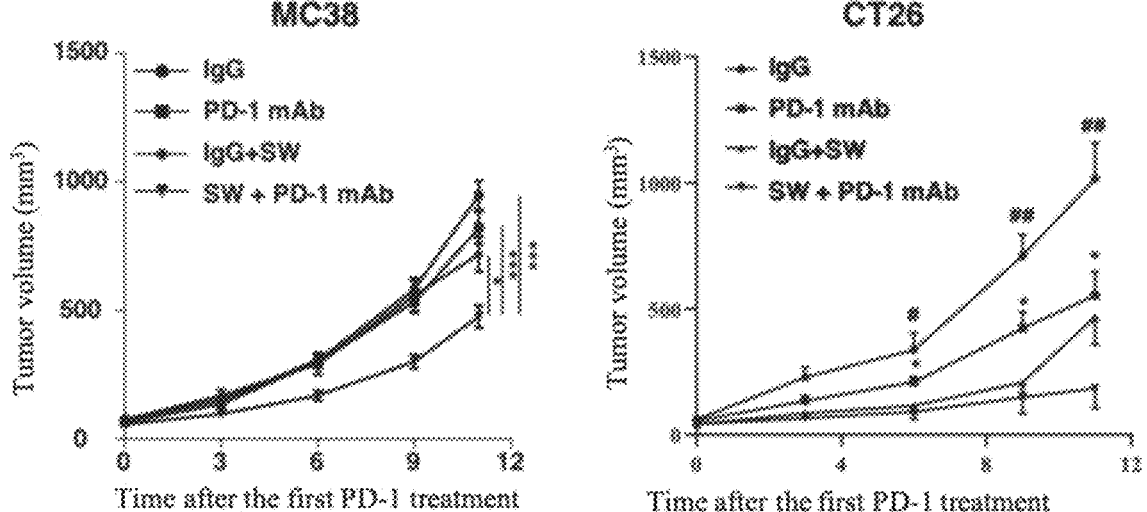
FIG. 2 shows tumor volume change curves; MC38 tumor model (left), CT26 tumor model (right).
Figure 3:
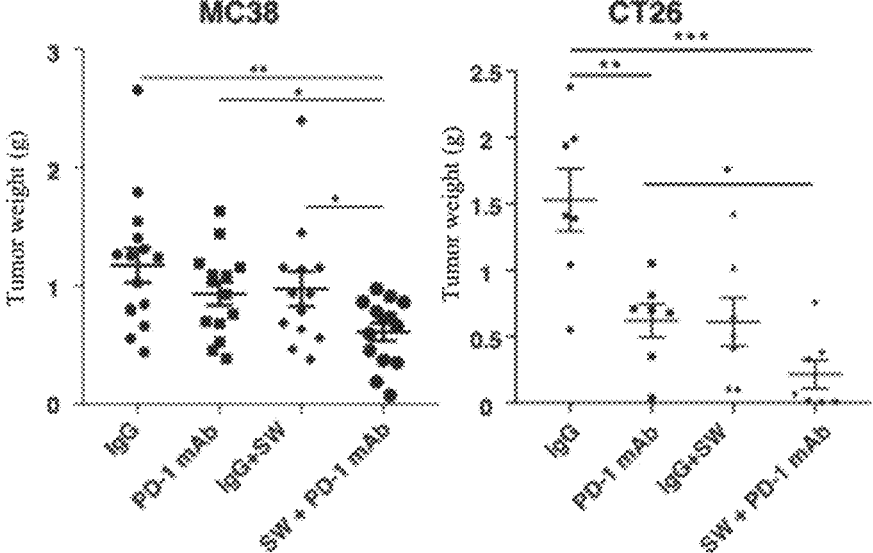
FIG. 3 shows tumor weight statistics; MC38 tumor model (left), CT26 tumor model (right).

As shown in FIG. 2 and FIG. 3, which are the tumor volume change curves and tumor weight statistics, respectively, the results show that in the MC38 and CT26 colon cancer mouse models, compared to the placebo treatment group (IgG) and the single-agent ICI group (PD-1 mAb), the combination therapy group (PD-1 mAb+SW) shows significant and substantial tumor reduction (p<0.01), proving that *Sutterella wadsworthensis* is capable of enhancing the antitumor effect of PD-1 mAb.

Figure 4:
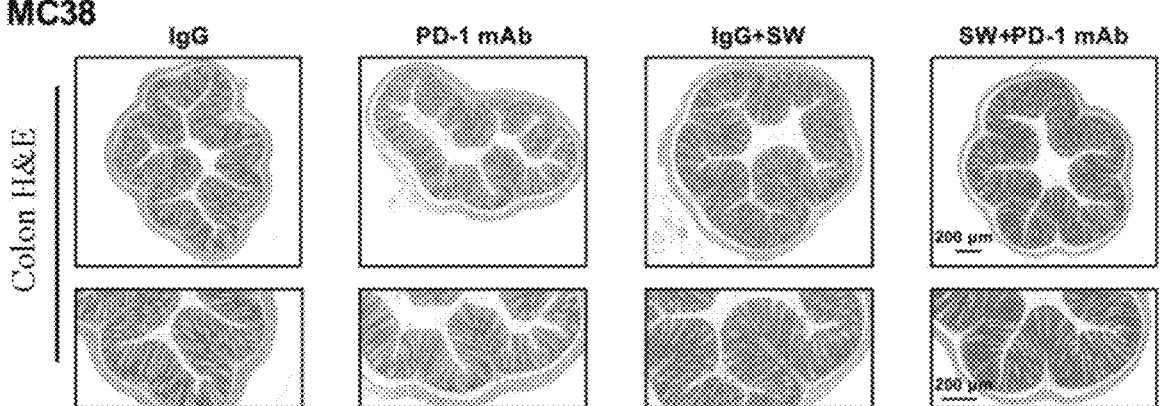
FIG. 4 shows hematoxylin-eosin (HE) staining images of gut tissues from MC38 tumor model mice (day 18).
Figure 5A:
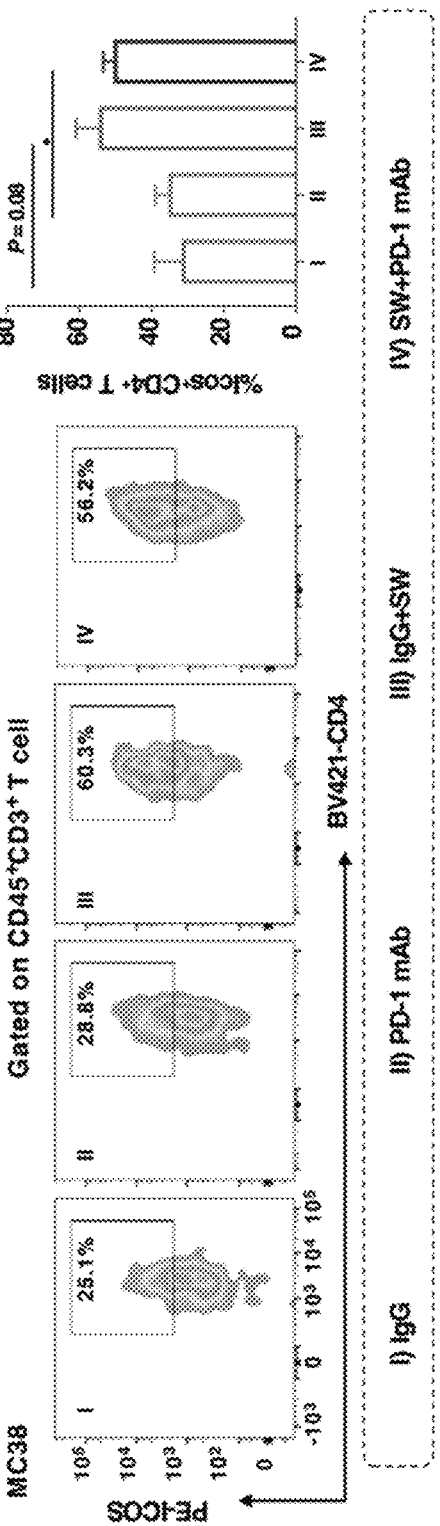
FIG. 5A shows $CD4^+$ inducible T cell costimulator (ICOS)+T cell proportions in MC38 model mouse tumor tissue.
Figure 5B:
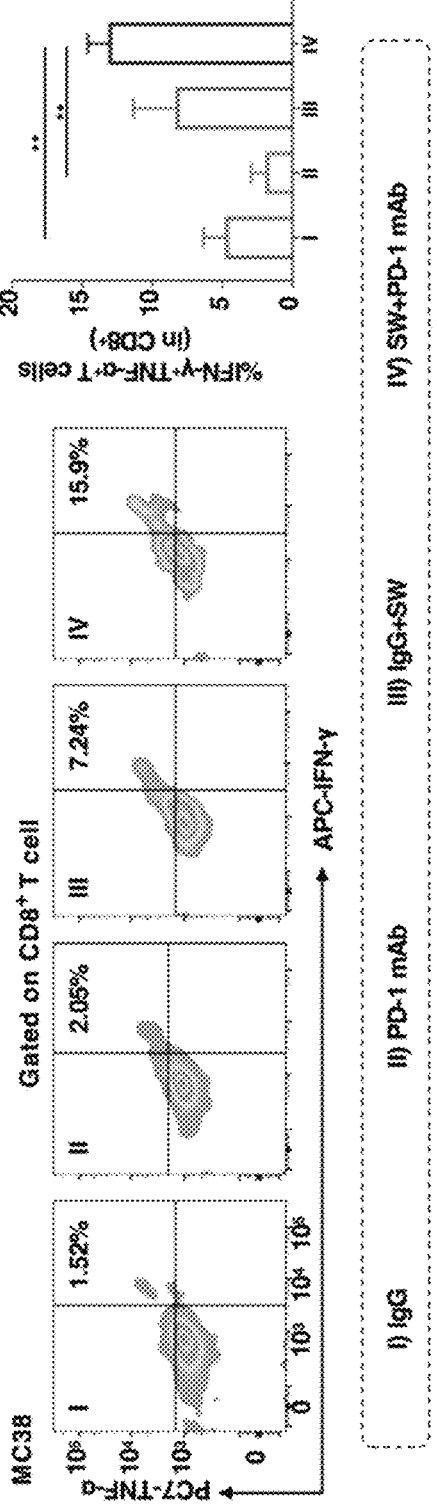
FIG. 5B shows $CD8^+IFN-\gamma$+tumor necrosis factor-alpha $(TNF-\alpha)$+T cell proportions in MC38 model mouse tumor tissue.
Figure 5C:
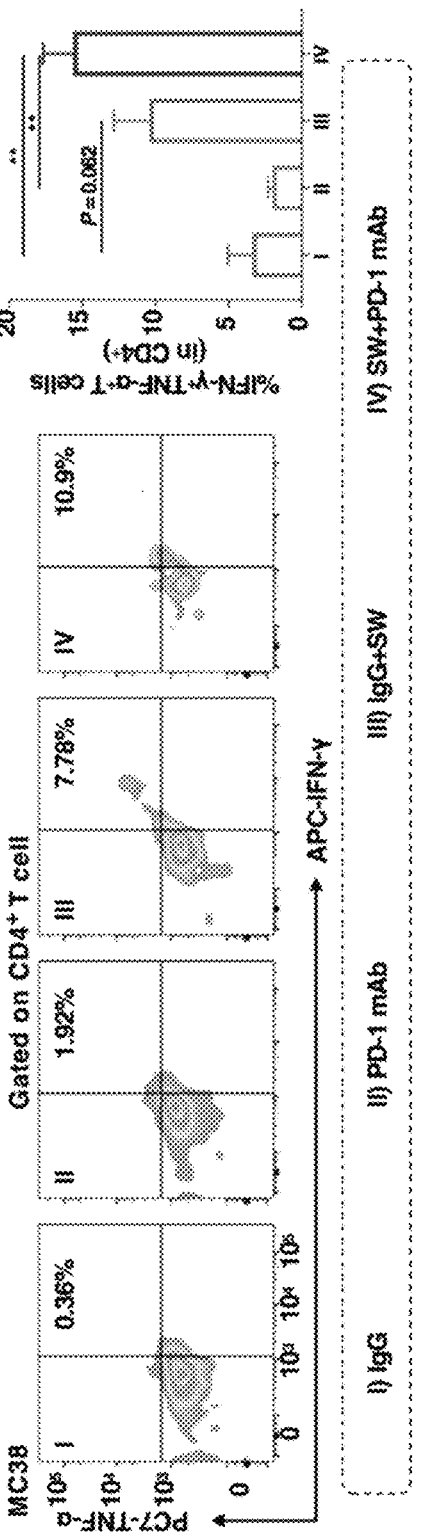
FIG. 5C shows $CD4^+IFN-\gamma$+$TNF-\alpha$+T cell proportions in MC38 model mouse tumor tissue.
Figure 5D:
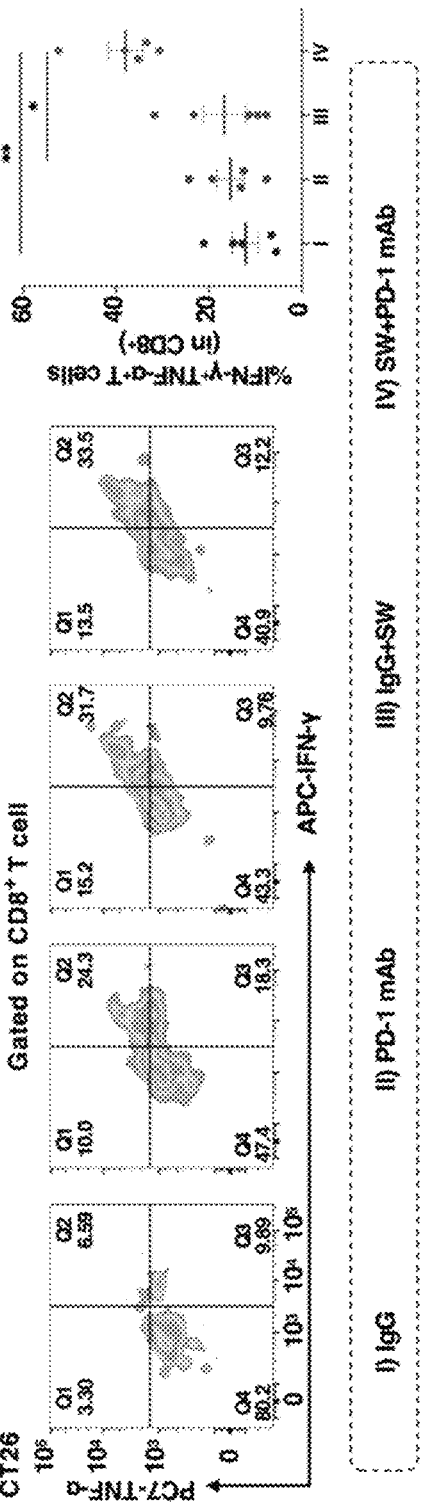
FIG. 5D shows $CD8^+IFN-\gamma$+$TNF-\alpha$+T cell proportions in CT26 model mouse tumor tissue.
Figure 5E:
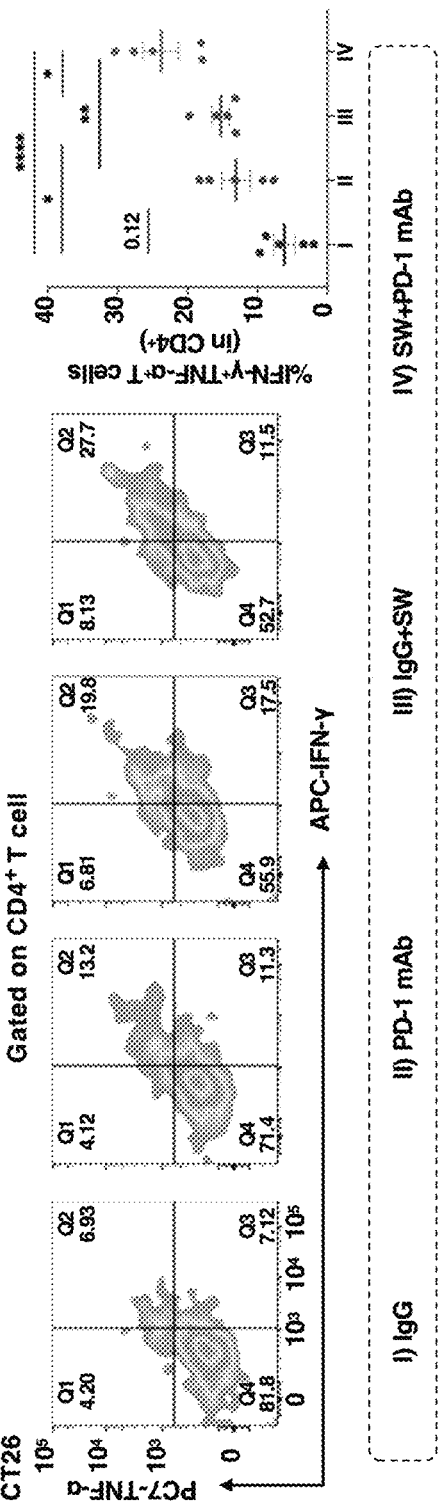
FIG. 5E shows $CD4^+IFN-\gamma$+$TNF-\alpha$+T cell proportions in CT26 model mouse tumor tissue.

The HE staining results of gut tissue sections from the MC38 mouse model at the experimental endpoint are shown in FIG. 4. The results show that neither the *Sutterella wadsworthensis* single bacterium group (IgG+SW) nor the combination therapy group (PD-1 mAb+SW) shows any signs of enteritis, proving the safety of oral gastrointestinal administration of *Sutterella wadsworthensis*.

As shown in FIG. 5A-FIG. 5E, the results of multicolor flow cytometry staining of MC38 (FIG. 5A-FIG. 5C) and CT26 (FIG. 5D-FIG. 5E) mouse tumor tissues at the experimental endpoints are presented. The results show that the *Sutterella wadsworthensis* single bacterium group (IgG+SW) significantly increases the infiltration of CD4⁺ ICOS+T cells in the tumor tissue. Compared to the single-agent ICI group (PD-1 mAb), the combination therapy group (PD-1 mAb+SW) also shows significantly increased infiltration of CD4⁺ ICOS+T cells in the tumor tissue. Additionally, in both the MC38 and CT26 mouse tumor models, compared to the single-agent ICI group (PD-1 mAb), the combination therapy group (PD-1 mAb+SW) shows increased CD8⁺ IFN-γ+TNF-α+ and CD4⁺ IFN-γ+TNF-α+T cells in the tumor tissue, confirming that *Sutterella wadsworthensis* may enhance the anti-tumor immune response of PD-1 mAb. Compared to the placebo treatment group (IgG), the *Sutte-*

*rella wadsworthensis* single bacterium group (IgG+SW) shows a trend of increased infiltration of CD8⁺ IFN-γ+TNF-α+T cells and CD4⁺ IFN-γ+TNF-α+T cells in the tumor, confirming the systemic immune regulatory effect of oral administration of *Sutterella wadsworthensis*.

Figure 6:
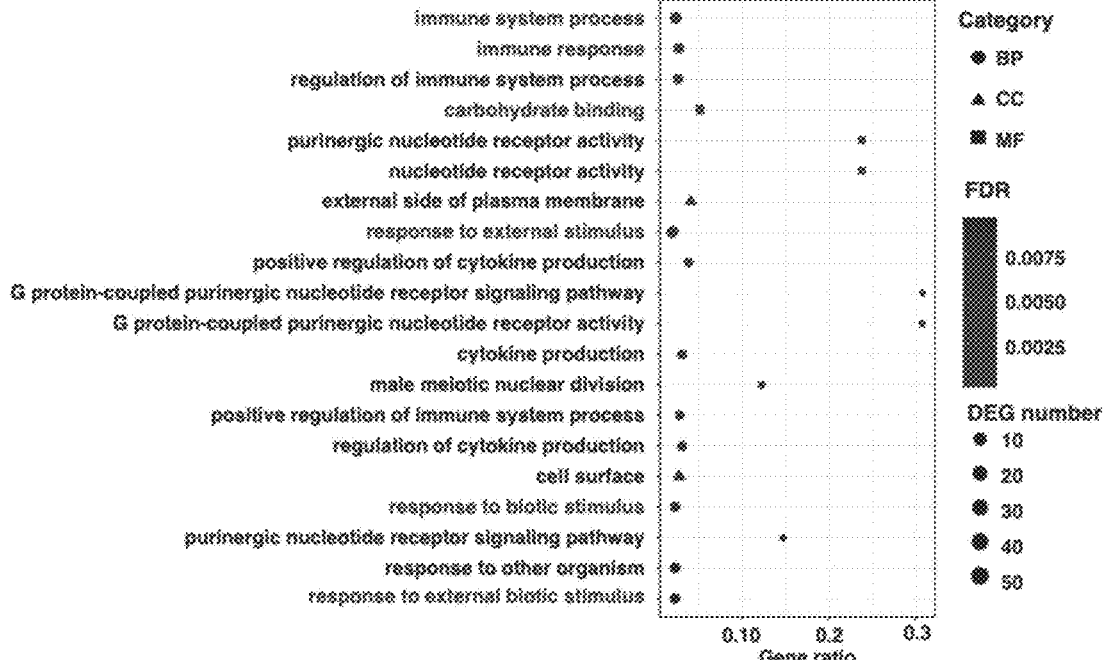
FIG. 6 shows RNA sequencing (RNA-seq) results of tumor tissues from the MC38 tumor model mice (day 18).

The RNA-seq results of mouse tumor tissues are shown in FIG. 6. The results show that compared to the single-agent ICI group (PD-1 mAb), the combination therapy group (PD-1 mAb+SW) exhibits activated anti-tumor immune response signals, indicating that oral administration of *Sutterella wadsworthensis* significantly enhances the anti-tumor immune response during ICI therapy.

Embodiment 2: *Sutterella wadsworthensis* as an Endogenous Gut Commensal Bacterium in Humans 1. Experimental Methods The GMrepo public database is used to analyze human gut metagenomic datasets, which includes a total of 2676 human fecal samples and involves 14 different types of populations. Metagenomic sequencing technology may achieve species-level identification of human gut microbiota.

The 14 different types of populations include: 1) healthy individuals; 2) diarrhea; 3) inflammatory bowel disease (IBD); 4) colorectal cancer (CRC); 5) autism spectrum disorder (ASD); 6) liver cirrhosis; 7) cardiovascular disease (CVD); 8) type 1 diabetes (TID); 9) rheumatoid arthritis (AR); 10) type 2 diabetes (T2D); 11) non-alcoholic fatty liver disease (NAFLD); 12) Parkinson's disease (PD); 13) hypertension; 14) metagenomic data of gut microbiota in renal cell carcinoma patients before receiving ICIs treatment.

The number of samples from the relevant population types is shown in Table 2.

TABLE 2

Human gut metagenomic public dataset

| Group | Healthy | Diarrhea | IBD | CRC | ASD | Liver Cirrhosis | CVD |
|---|---|---|---|---|---|---|---|
| Number of samples | 1861 | 27 | 35 | 265 | 29 | 25 | 29 |
| Group | T1D | AR | T2D | NAFLD | PD | Hypertension | RCC_ICIs |
| Number of samples | 24 | 33 | 68 | 52 | 88 | 39 | 101 |

2. Experimental Results

Figure 7:
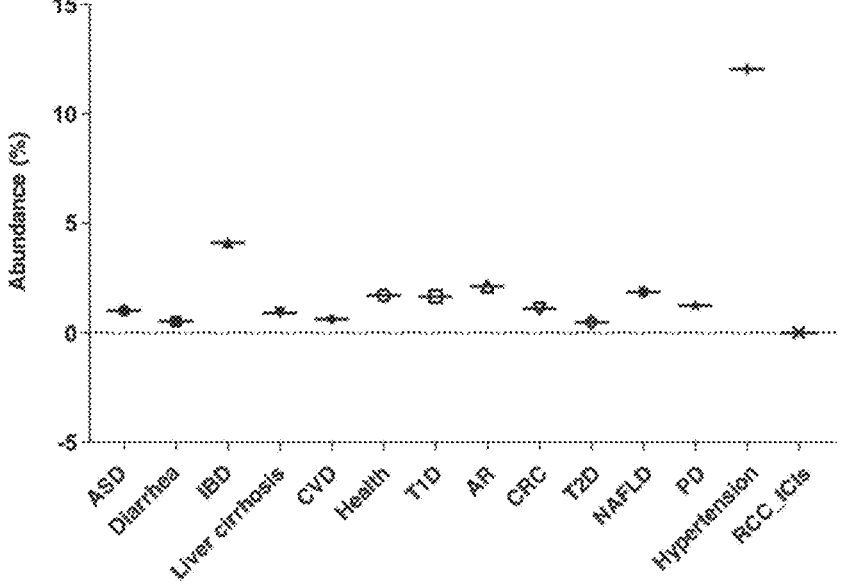
FIG. 7 shows distribution and relative abundance of *Sutterella wadsworthensis* in different populations.

As shown in FIG. 7 and Table 3, the results show that *Sutterella wadsworthensis* is present in different populations, with a relative abundance ranging from 0.47% to 12.5%, and there are differences in the relative abundance of *Sutterella wadsworthensis* among different populations. The relative abundance refers to the proportion of a particular bacterial species in the total bacterial species in the gut. Based on the estimate that the total number of bacterial species in the human gut is approximately $10^{14}$ CFU/mL, the number of *Sutterella wadsworthensis* in the human gut is approximately $10^{11}$ CFU/mL to $10^{13}$ CFU/mL.

TABLE 3

Relative abundance of *Sutterella wadsworthensis* in different populations

| Group | Average abundance of Waldesat bacteria (%) |
|---|---|
| Healthy | 1.703 |
| Diarrhea | 0.5156 |
| IBD | 4.123 |
| CRC | 1.094 |
| ASD | 1.010 |
| Liver Cirrhosis | 0.9004 |
| CVD | 0.6230 |
| T1D | 1.655 |
| AR | 2.124 |
| T2D | 0.4764 |
| NAFLD | 1.865 |
| PD | 1.250 |
| Hypertension | 12.05 |
| RCC_ICIs | 0.7114 |

Embodiment 3 The abundance of *Sutterella wadsworthensis* in gut is related to response to ICI therapy in patients with renal cell carcinoma 1. Experimental Methods The gut metagenomic public dataset PRJEB 22863 of renal cell carcinoma patients is analyzed, which includes 62 fecal samples from renal cell carcinoma (RCC) patients before receiving ICI therapy. The relationship between the baseline abundance of *Sutterella wadsworthensis* in the feces of RCC patients and their response to ICI therapy is established.

2. Experimental Results

Figure 8A:
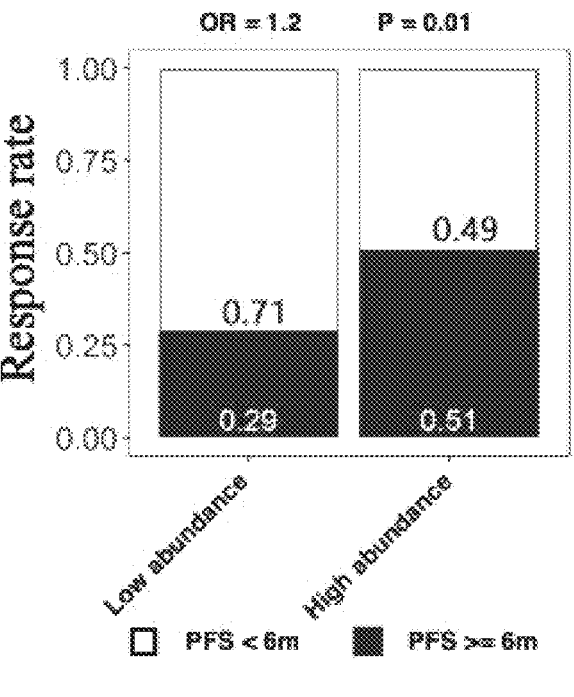
FIG. 8A shows a relationship between abundance of *Sutterella wadsworthensis* and an efficacy of ICIs in renal cell carcinoma patients in progression-free survival.
Figure 8B:
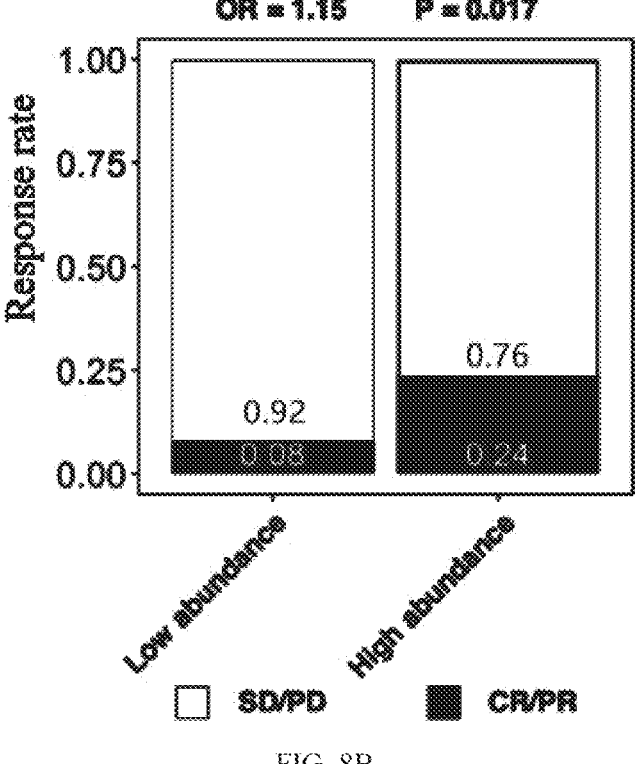
FIG. 8B shows treatment effect, where SD is stable disease, CR is complete response, PD is progressive disease, and PR is partial response.

As shown in FIG. 8, the results show that renal cell carcinoma patients with high gut abundance of *Sutterella wadsworthensis* have a higher proportion of progression-free survival (PFS) greater than or equal to 6 months, better disease control, and higher response rates.

The above-described embodiments are only illustrative of the preferred embodiments of the present disclosure and do not limit the scope of the present disclosure. Without departing from the spirit of the present disclosure, various modifications and improvements made by those skilled in the art to the technical solutions of the present disclosure shall fall within the scope of protection defined by the claims of the present disclosure.

What is claimed is:

1. A pharmaceutical composition, comprising an effective dose of *Sutterella wadsworthensis* in combination with an immune checkpoint inhibitor, wherein a deposit number of the *Sutterella wadsworthensis* is DSM NO: 14016, the immune checkpoint inhibitor is a PD-1 monoclonal antibody, the *Sutterella wadsworthensis* is a live bacterium, and the pharmaceutical composition is for use in treating colon cancer.

* * * * *

SEQUENCE LISTING

```
Sequence total quantity: 1
SEQ ID NO: 1              moltype = DNA  length = 1462
FEATURE                   Location/Qualifiers
source                    1..1462
                          mol_type = other DNA
                          organism = synthetic construct
SEQUENCE: 1
ctttacacat gcaagtcgaa cggcagcgcg gggagcttgc tccctggcgg cgagtggcgc    60
acgggtgagt aatacatcgg aacgtgtctt ctagtggggg ataactgccc gaaagggcag   120
ctaataccgc atgagacctg agggtgaaag cggggatcg caagacctcg cgctggaaga   180
gcggccgatg tccgattagc tagttggtga ggtaaaggct caccaaggcg acgatcggta   240
```

-continued

```
gctggtctga gaggacgacc agccacactg ggactgagac acggcccaga ctcctacggg   300
aggcagcagt ggggaatttt ggacaatggg ggcaaccctg atccagccat gccgcgtgca   360
ggatgaaggt cttcggattg taaactgctt ttgtcaggga cgaaaaggga tgcgataaca   420
ccgcattccg ctgacggtac ctgaagaata agcaccggct aactacgtgc cagcagccgc   480
ggtaatacgt agggtgcaag cgttaatcgg aattactggg cgtaaagcgt gcgcaggcgg   540
ttctgtaaga tagatgtgaa atccccgggc tcaacctggg aattgcatat atgactgcag   600
gacttgagtt tgtcagagga gggtggaatt ccacgtgtag cagtgaaatg cgtagatatg   660
tggaagaaca ccgatggcga aggcagccct ctgggacatg actgacgctc atgcacgaaa   720
gcgtggggag caaacaggat tagataccct ggtagtccac gccctaaacg atgtctacta   780
gttgttgggg acgatagtcc ttggtaacgc agctaacgcg tgaagtagac cgcctgggga   840
gtacggtcgc aagattaaaa ctcaaaggaa ttgacgggga cccgcacaag cggtggatga   900
tgtggattaa ttcgatgcaa cgcgaaaaac cttacctagc cttgacatgc caggaaggcc   960
tgagagatca ggccgtgccc gcaagggaat ctggacacag gtgctgcatg gctgtcgtca  1020
gctcgtgtcg tgagatgttg ggttaagtcc cgcaacgagc gcaacccttg tcattagttg  1080
ctacgaaagg gcactctaat gagactgccg gtgacaaacc ggaggaaggt ggggatgacg  1140
tcaagtcctc atggccctta tggctagggc ctcacacgtc atacaatggt cggaacagag  1200
ggaagcgaag ccgcgaggtg aagccaatcc cagaaaccg atcgtagtcc ggattgcagt  1260
ctgcaactcg actgcatgaa gtcggaatcg ctagtaatcg cggatcagca tgccgcggtg  1320
aatacgttcc cgggtcttgt acacaccgcc cgtcacacca tggggagtgg ggttcaccag  1380
aagacgtttg cccaaccgaa aggaaggcgg cgtccacggt gggcttcatg actggggtga  1440
agtcgtaaca aggtaaccgt aa                                            1462
```